(12) United States Patent
Ferdosi et al.

(10) Patent No.: US 11,744,522 B2
(45) Date of Patent: *Sep. 5, 2023

(54) CONTINUOUS ASSESSMENT OF ECG SIGNAL QUALITY

(71) Applicant: Vital Connect, Inc., San Jose, CA (US)

(72) Inventors: Nima Ferdosi, San Jose, CA (US); Ravi Narasimhan, Sunnyvale, CA (US)

(73) Assignee: Vital Connect, Inc., San Jose, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/364,167

(22) Filed: Jun. 30, 2021

(65) Prior Publication Data
US 2021/0393209 A1  Dec. 23, 2021

Related U.S. Application Data

(62) Division of application No. 13/604,287, filed on Sep. 5, 2012, now Pat. No. 11,076,810.

(51) Int. Cl.
*A61B 5/00* (2006.01)
*A61B 5/30* (2021.01)

(52) U.S. Cl.
CPC .......... *A61B 5/7221* (2013.01); *A61B 5/0006* (2013.01); *A61B 5/30* (2021.01); *A61B 5/7207* (2013.01)

(58) Field of Classification Search
None
See application file for complete search history.

(56) References Cited

U.S. PATENT DOCUMENTS

| 11,076,810 | B2 * | 8/2021 | Ferdosi | ............... A61B 5/7221 |
| 2001/0019633 | A1 | 9/2001 | Tenze et al. | |

(Continued)

FOREIGN PATENT DOCUMENTS

| EP | 2430975 A1 | 3/2012 |
| JP | H07136142 A | 5/1995 |

(Continued)

OTHER PUBLICATIONS

R. Ferzli, et al "Efficient Implementation of Kurtosis Based No Reference Image Sharpness Metric", Proceedings of SPIE, vol. 7532, Jan. 26, 2010, 12 pages.

(Continued)

*Primary Examiner* — Catherine M Voorhees
*Assistant Examiner* — Elizabeth K So
(74) *Attorney, Agent, or Firm* — Shih IP Law Group, PLLC (57) ABSTRACT

A method and system for assessing an electrocardiogram (ECG) signal quality are disclosed. In a first aspect, the method comprises determining a Kurtosis calculation of the ECG signal and determining whether the Kurtosis calculation satisfies a first threshold to continuously assess the ECG signal quality. In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to determine a Kurtosis calculation of the ECG signal and to determine whether the Kurtosis calculation satisfies a first threshold to continuously assess the ECG signal quality.

6 Claims, 6 Drawing Sheets

(56) References Cited

U.S. PATENT DOCUMENTS

| | | |
|---|---|---|
| 2005/0124904 A1 | 6/2005 | Roteliuk |
| 2005/0267377 A1 | 12/2005 | Marossero et al. |
| 2009/0076410 A1 | 3/2009 | Libbus et al. |
| 2010/0302083 A1 | 12/2010 | Helfenstein |
| 2011/0263994 A1 | 10/2011 | Burns et al. |
| 2012/0071730 A1 | 3/2012 | Romero |
| 2013/0070792 A1 | 3/2013 | Shoaib et al. |
| 2013/0144130 A1 | 6/2013 | Russell et al. |

FOREIGN PATENT DOCUMENTS

| | | |
|---|---|---|
| JP | 2005253610 A | 9/2005 |
| JP | 2010029656 A | 2/2010 |
| WO | 2009036369 A1 | 3/2009 |
| WO | 2011006356 A1 | 1/2011 |

OTHER PUBLICATIONS

Extended European Search Report (EESR), dated Jan. 27, 2016.
Japanese Office Action dated Mar. 29, 2016.
International Search Report and the Written Opinion for International Application No. PCT/US2013/058217, dated Feb. 7, 2014.

\* cited by examiner

CONTINUOUS ASSESSMENT OF ECG SIGNAL QUALITY

CROSS-REFERENCE TO RELATED APPLICATIONS

This application is a Divisional of U.S. application Ser. No. 13/604,287, filed Sep. 5, 2012, U.S. Pat. No.: 11,076,810, issued on Aug. 3, 2021, which is incorporated herein by reference in its entirety.

FIELD OF THE INVENTION

The present invention relates to sensor devices, and more particularly, to a sensor device utilized to continually assess ECG signal quality.

BACKGROUND

A person's electrocardiogram (ECG) measurement is one of the vital signs commonly used in clinical practices to measure heart and overall health. By attaching electrodes on the user's body, an ECG signal can be measured. However, several ambient noises such as motion artifacts and baseline wander can result from the movement of the user and are thus mixed in with the ECG signal. In certain cases, these noise sources are strong enough to overwhelm the ECG signal completely and make extraction of heart rate and other physiological data measurements unreliable.

These issues limit the continuous monitoring and accurate measuring of a person's ECG signal. Therefore, there is a strong need for a cost-effective solution that overcomes the above issues by continuously assessing ECG signal quality and detecting situations when strong noise has rendered the sensed ECG signal unreliable. The present invention addresses such a need.

SUMMARY OF THE INVENTION

A method and system for assessing an electrocardiogram (ECG) signal quality are disclosed. In a first aspect, the method comprises determining a Kurtosis calculation of the ECG signal and determining whether the Kurtosis calculation satisfies a first threshold to continuously assess the ECG signal quality.

In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to determine a Kurtosis calculation of the ECG signal and to determine whether the Kurtosis calculation satisfies a first threshold to continuously assess the ECG signal quality.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

The present invention relates to sensor devices, and more particularly, to a sensor device utilized to continually assess ECG signal quality. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

To overcome a lack of reference ECG signals available for conventional signal to noise measurements, the present invention utilizes statistical properties of the motion artifacts, background noise, and the ECG signal to continuously assess the quality of the ECG signal. A method and system in accordance with the present invention allows for the continuous quality assessment of an electrocardiogram (ECG) signal. By connecting a sensor device to the user through at least one electrode, a single-lead, bipolar analog ECG signal of the user is measured. The analog ECG signal is then sampled and converted to a digital domain through an analog-to-digital converter (ADC) to eliminate motion artifacts and noise. A Kurtosis calculation of the digital ECG signal is determined and compared to a first threshold to continuously assess the quality of the ECG signal. If a portion of the ECG signal is determined to be unreliable, that portion can be ignored.

One of ordinary skill in the art readily recognizes that a variety of sensor devices can be utilized for the measuring of the ECG data signal segment including portable wireless sensor devices with embedded circuitry in a patch form factor and that would be within the spirit and scope of the present invention.

To describe the features of the present invention in more detail, refer now to the following description in conjunction with the accompanying Figures.

Figure 1:
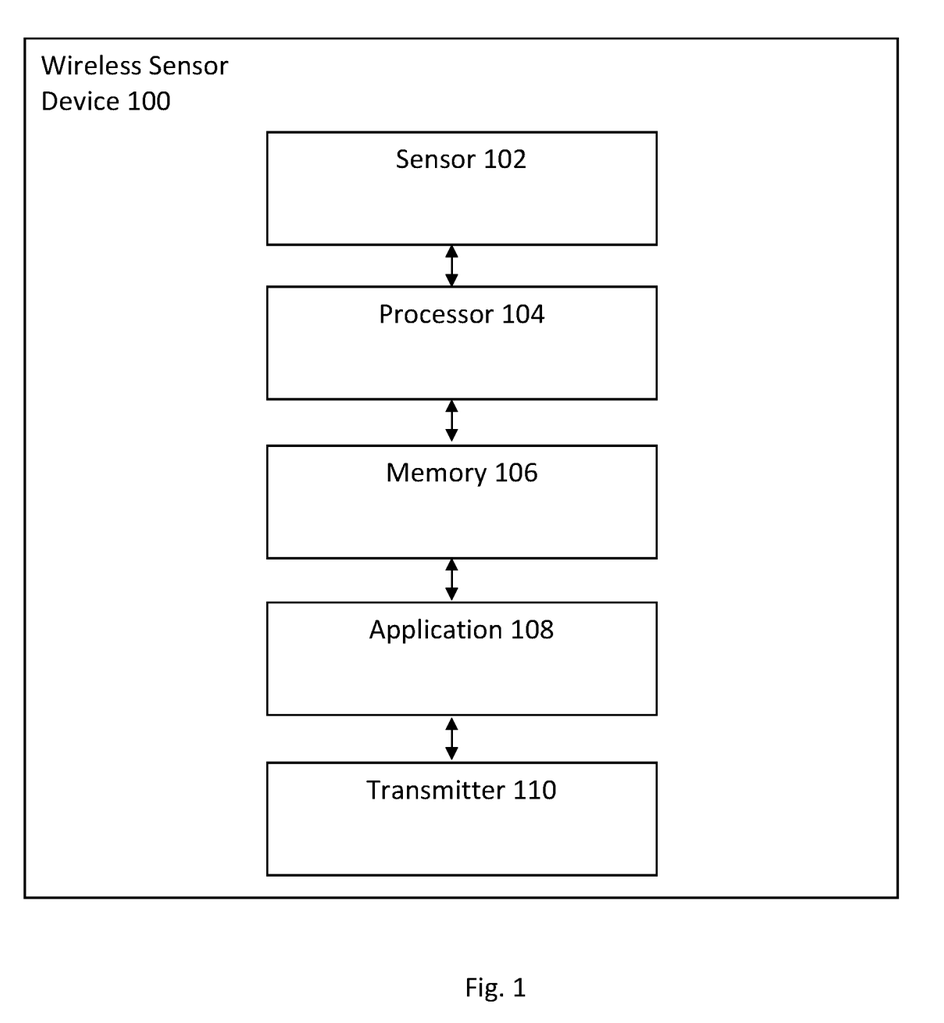
FIG. 1 illustrates a wireless sensor device in accordance with an embodiment.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The sensor 102 obtains data from the user and transmits the data to the memory 106 and in turn to the application 108. The processor 104 executes the application 108 to process ECG signal information of the user. The information is transmitted to the transmitter 110 and in turn relayed to another user or device.

In one embodiment, the sensor 102 comprises two electrodes and the processor 104 is a microprocessor. One of ordinary skill in the art readily recognizes that a variety of devices can be utilized for the processor 104, the memory 106, the application 108, and the transmitter 110 and that would be within the spirit and scope of the present invention.

Figure 2:
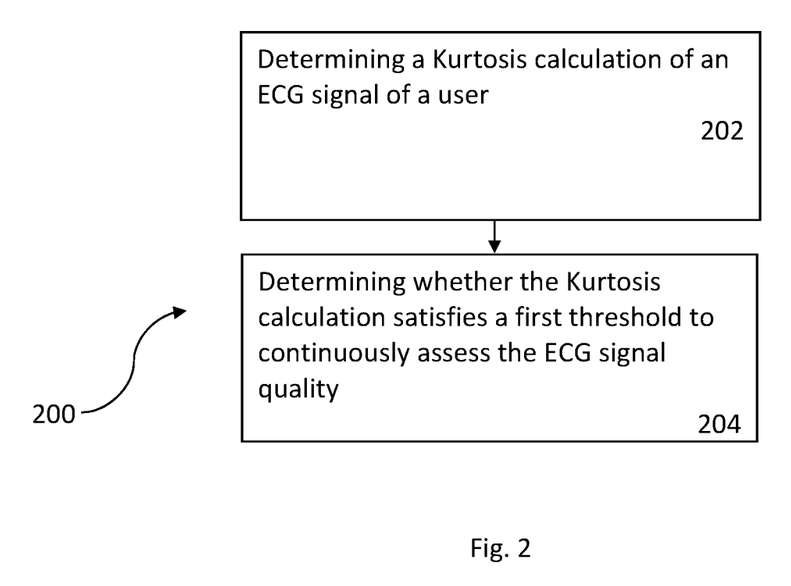
FIG. 2 illustrates a flow chart of a method in accordance with an embodiment.

FIG. 2 illustrates a flow chart of a method 200 in accordance with an embodiment. Referring to FIGS. 1 and 2 together, the method 200 comprises the wireless sensor device 100 determining a Kurtosis calculation of an ECG signal of a user, via step 202. The method includes determining whether the Kurtosis calculation satisfies a first threshold to continuously assess the ECG signal quality, via step 204. In this embodiment, the sensor 102 that is housed within the wireless sensor device 100 measures the ECG signal of the user at a variety of sampling frequencies prior to the Kurtosis calculation. In another embodiment, notification information of the Kurtosis calculation is relayed by the wireless sensor device 100 to another user or device.

An ECG signal has a sharp peak in the probability density function in contrast to background noise which has a flatter distribution. The noisier the ECG signal, the flatter the distribution of the combination of ECG signal and noise. In one embodiment, a Kurtosis algorithm is utilized to measure sharp peaks of the distribution of a random variable. Kurtosis of a random variable (x) is defined as Kurtosis(x)=(E(x−m)$^4$)/(E((x−m)$^2$)$^2$), where E(x) is the expected value of the random variable x and m=E(x). Calculation of the Kurtosis of the ECG signal utilizing the above-mentioned equation is expensive with regards to both computation power and storage memory.

One of ordinary skill in the art readily recognizes that an ECG signal has a high Kurtosis including but not limited to a value greater than approximately 10, a pure Gaussian signal has a Kurtosis including but not limited to a value of approximately 3, and a motion artifact noise corrupting the ECG signal has a Kurtosis including but not limited to a value of approximately between 2 and 5, and that would be within the spirit and scope of the present invention.

Figure 3:
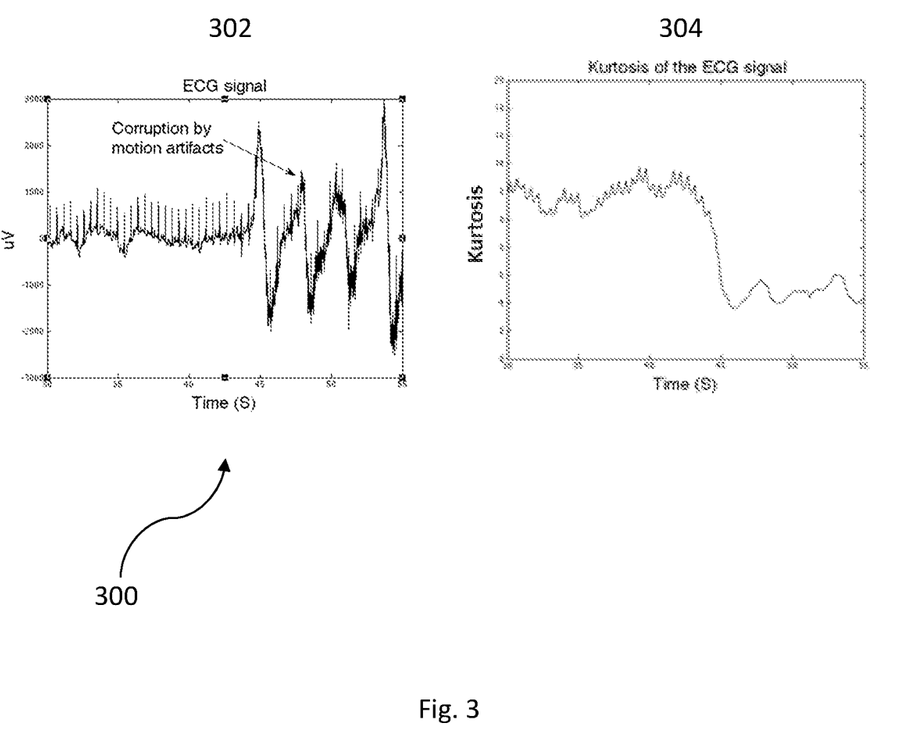
FIG. 3 illustrates a diagram of Kurtosis of an ECG signal in accordance with an embodiment.

FIG. 3 illustrates a diagram 300 of Kurtosis of an ECG signal in accordance with an embodiment. In the diagram 300, the left FIG. 302 shows an ECG signal corrupted by motion artifacts and the right FIG. 304 shows Kurtosis of an ECG signal that decreases when combined with motion artifact and noise corruption.

Figure 4:
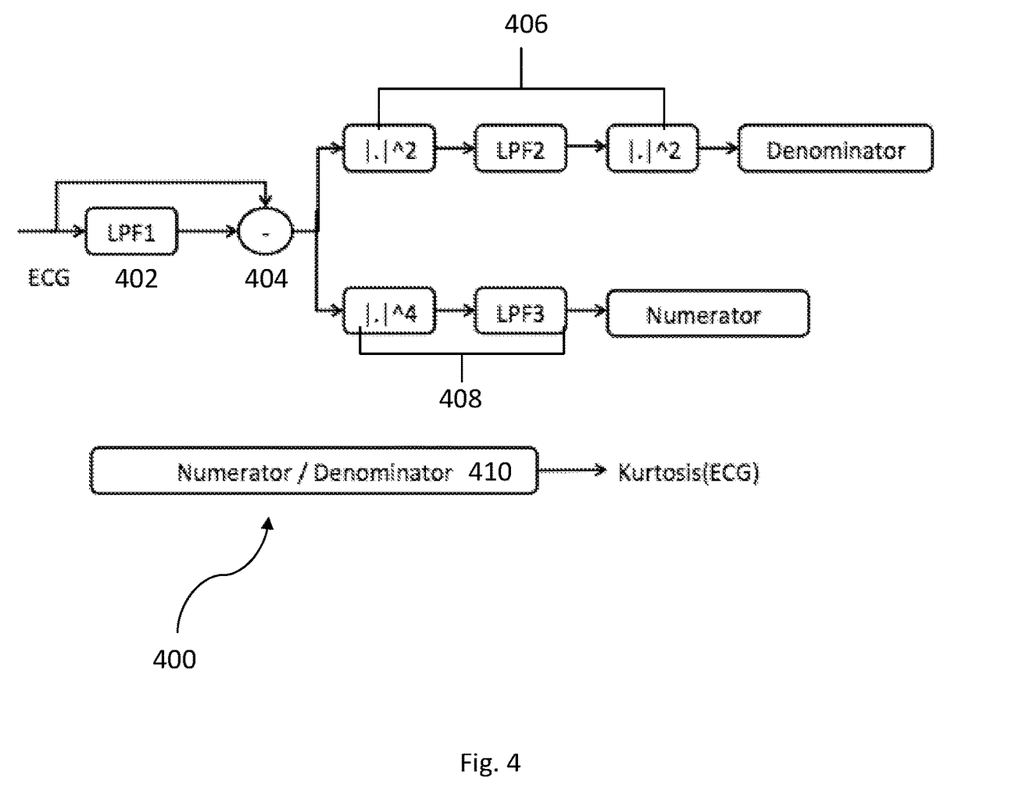
FIG. 4 illustrates a more detailed flow chart of a method in accordance with an embodiment.

FIG. 4 illustrates a more detailed flow chart of a method 400 in accordance with an embodiment. In this embodiment, computation of the expected value E(.) is approximated by passing the ECG signal through a one pole, low pass Infinite Impulse Response (IIR) filter with appropriate parameters. The approximation reduces both the computation power and storage memory requirements of the Kurtosis calculation. One of ordinary skill in the art readily recognizes that although an IIR filter is utilize, the ECG signal can be passed through a variety of filters and that would be within the spirit and scope of the present invention.

In the method 400, a mean of the ECG signal is calculated using a first low pass filter (LPF1), via 402. The mean is removed from the ECG signal, via 404. A Second moment (1.1$^2$) is approximated using a second low pass filter (LPF2) and squared to output a denominator value, via 406, and a Fourth moment (1.1$^4$) is approximated using a third low pass filter (LPF3) to output a numerator value, via 408. A Kurtosis of the ECG signal is calculated by dividing the numerator value by the denominator value, via 410.

Figure 5:
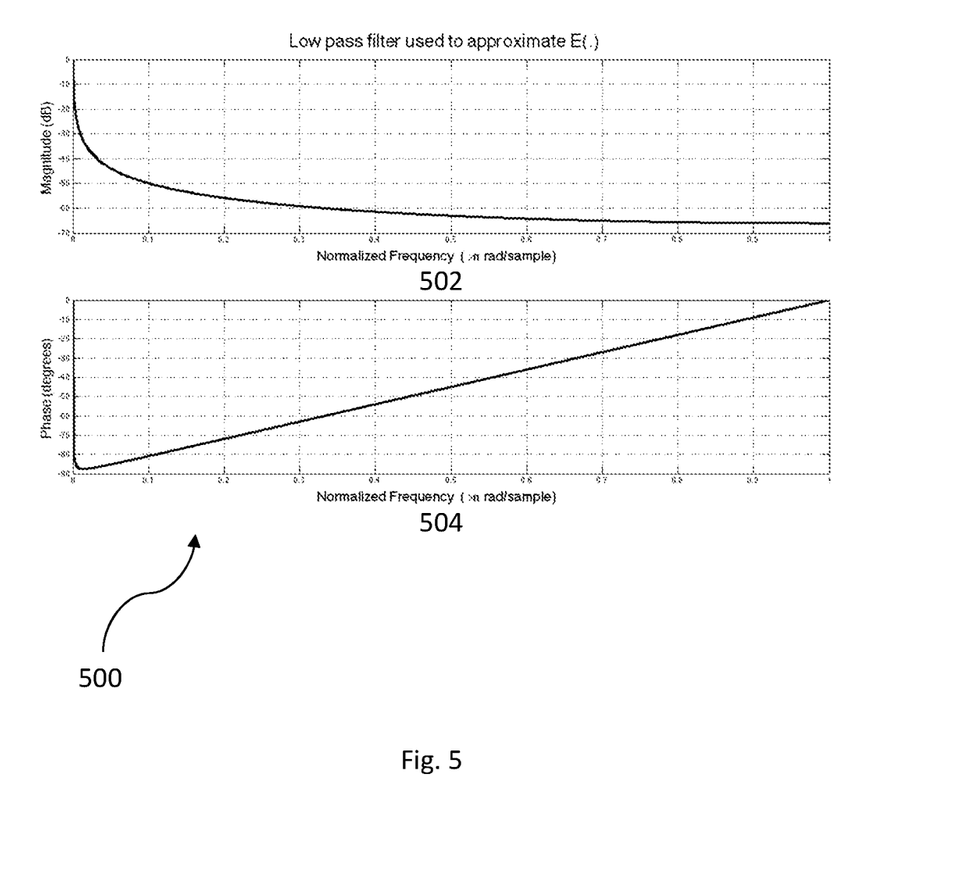
FIG. 5 illustrates a diagram of low pass IIR filter parameters in accordance with an embodiment.

FIG. 5 illustrates a diagram 500 of low pass IIR filter parameters in accordance with an embodiment. In the diagram 500, the top FIG. 502 shows a magnitude (dB) plot against a normalized frequency of the low pass IIR filter used to approximate E(.) and the bottom FIG. 504 shows a phase (degrees) plot against a normalized frequency of the low pass IIR filter used to approximate E(.).

Figure 6:
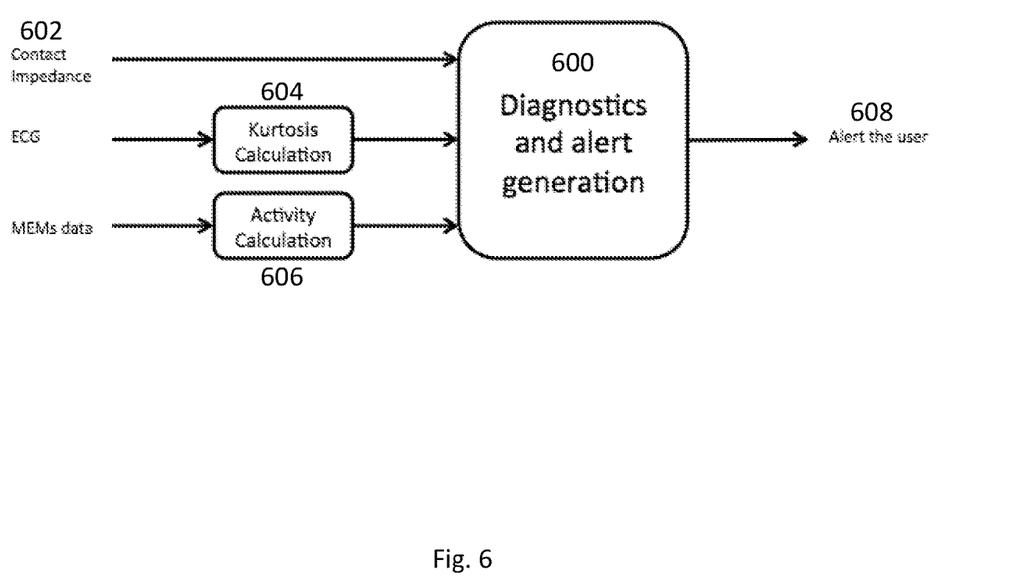
FIG. 6 illustrates a diagnostic unit in accordance with an embodiment.

FIG. 6 illustrates a diagnostic unit 600 in accordance with an embodiment. In one embodiment, the diagnostic unit 600 is embedded within the wireless sensor device 100 of FIG. 1 to determine the source of the noise and generate appropriate alerts. The diagnostic unit 600 receives a variety of information including but not limited to a contact impedance determination 602 between the user's skin and the wireless sensor device 100, a Kurtosis calculation 604 of an ECG signal detected by the wireless sensor device 100, and a user activity level calculation 606 detected by the wireless sensor device 100 via microelectromechanical systems (MEMS) data. In this embodiment, after receiving this variety of information, the diagnostic unit generates a variety of alerts 608 that are transmitted to another user or device.

In one embodiment, if the Kurtosis calculation of the ECG signal is less than a first threshold (indicative of poor ECG quality), and the contact impedance is less than a second threshold (indicative of good electrode skin contact), and the user activity level is greater than a third threshold (indicative of the user being physically active), then the diagnostic unit 60 alerts the user of the wireless sensor device 100 via the variety of alerts 608 that the ECG signal quality is low because of motion artifacts and noise.

One of ordinary skill in the art readily recognizes that the first, second, and third thresholds can be labeled in a variety of ways including but not limited to the first threshold being labeled threshold_K1 (Kurtosis calculation) with a value of 10, the second threshold being labeled threshold_C (contact impedance determination) with a value of 1M ohms, and the third threshold being labeled threshold_A (user activity level calculation) with a value of 0.3 (normalized to standard gravity, g) and that would be within the spirit and scope of the present invention.

In a second embodiment, if the Kurtosis calculation of the ECG signal is less than threshold_K1 (indicative of poor ECG quality), and the contact impedance is greater than threshold_C (indicative of poor electrode skin contact), and the user activity level is less than threshold_A (indicative of the user being physically inactive), then the diagnostic unit 60 alerts the user via the variety of alerts 608 that the ECG signal quality is low because of improper wireless sensor device 100 contact to skin.

In a third embodiment, if the Kurtosis calculation of the ECG signal is less than threshold_K1 (indicative of poor ECG quality), and the contact impedance is greater than threshold_C (indicative of poor electrode skin contact), and the user activity level is greater than threshold_A (indicative of the user being physically active), then the diagnostic unit 600 alerts the user via the variety of alerts 608 that the ECG signal quality is low because of both motion artifacts and improper wireless sensor device 100 contact to skin.

In a fourth embodiment, if the Kurtosis calculation of the ECG signal is greater than threshold_K1 (indicative of good ECG quality), then the diagnostic unit 600 alerts the user via the variety of alerts 608 that ECG signal quality is high and heart function computations can be completed.

As above described, the method and system allow for assessing an electrocardiogram (ECG) signal quality. By attaching a wireless sensor device to the user to measure the ECG signal, calculating a Kurtosis of the ECG signal utilizing efficient power consumption and storage memory techniques, and measuring other metrics such as user activity and contact impedance, a cost-effective and continuous ECG signal quality assessment system is achieved.

A method and system for assessing an electrocardiogram (ECG) signal quality has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for assessing an electrocardiogram (ECG) signal quality, wherein the ECG signal of a user is measured using a wireless sensor device coupled to the user via at least one electrode, the method comprising:
    approximating an expected value E(.) using a plurality of filters, each comprising a one pole, low pass Infinite Impulse Response filter, to determine a Kurtosis calculation of an ECG signal by:
        determining a mean of the ECG signal using a first low pass filter,
    removing the mean determined using the first low pass filter from the ECG signal,
        approximating a Second moment using a second low pass filter after removing the mean from the ECG signal,
        squaring the Second moment after approximating a Second moment using a second low pass filter to output a denominator value,
    approximating a Fourth moment using a third low pass filter after removing the mean from the ECG signal to output a numerator value, and
        determining the Kurtosis calculation by dividing the numerator value by the denominator value;
        determining whether the Kurtosis calculation satisfies a first threshold to continuously assess the ECG signal quality;
    determining contact impedance between the wireless sensor device and the user; and determine whether the contact impedance satisfies a second threshold, wherein quality of electrode skin contact is assessed;
    determining a user activity level via at least one MEMS sensor of the wireless sensor device; and determine whether the user activity level satisfies a third threshold, wherein extent of user activity is assessed;
    determining source of noise based on comparing: Kurtosis calculation with the first threshold, contact impedance with the second threshold, and user activity level with the third threshold; and
    generating appropriate alerts, wherein the alerts include information regarding quality of the ECG signal and source of the noise.

2. The method of claim 1, further comprising:
    determining a user activity level via the at least one MEMS sensor of the wireless sensor device; and
    determining whether the user activity level satisfies a third threshold, wherein extent of user activity is assessed.

3. The method of claim 1, wherein generating appropriate alerts includes alerting the user that the quality of the ECG signal is low due to improper skin contact of the wireless sensor device in response to the Kurtosis calculation being less than the first threshold, the contact impedance being greater than the second threshold, and the user activity level being less than the third threshold.

4. The method of claim 1, wherein generating appropriate alerts includes alerting the user that the quality of the ECG signal is low due to motion artifacts and improper skin contact of the wireless sensor device in response to the Kurtosis calculation being less than the first threshold, the contact impedance being greater than the second threshold, and the user activity level being greater than the third threshold.

5. The method of claim 1, wherein generating appropriate alerts includes alerting the user that the quality of the ECG signal is high enough to allow for heart function computation in response to the Kurtosis calculation being greater than the first threshold.

6. The method of claim 1, wherein generating appropriate alerts includes alerting the user that the quality of the ECG signal is low due to motion artifacts in response to the Kurtosis calculation being less than the first threshold, the contact impedance being less than the second threshold, and the user activity level being greater than the third threshold.

* * * * *